United States Patent [19]

Haswell et al.

[11] Patent Number: 5,215,715
[45] Date of Patent: Jun. 1, 1993

[54] MICROWAVE HEATED DIGESTING SYSTEM FOR DIGESTING MATERIALS TO BE ANALYZED

[75] Inventors: Stephen J. Haswell, Cottingham; David A. Barclay, Stourbridge, both of England

[73] Assignee: CEM Corporation, Matthews, N.C.

[21] Appl. No.: 727,885

[22] Filed: Jul. 10, 1991

[51] Int. Cl.⁵ .............................................. G01N 1/00
[52] U.S. Cl. ........................................ 422/81; 422/21; 422/186; 436/52; 436/175; 436/177; 219/10.55 R; 219/10.55 M; 204/158.2; 204/157.43; 204/302; 204/308
[58] Field of Search ........................... 422/21, 81, 186; 436/52, 175, 177; 219/10.55 R, 10.55 M; 204/158.2, 157.43, 302, 308

[56] References Cited

U.S. PATENT DOCUMENTS 4,952,372  8/1990  Huber ................................ 436/52 X
4,978,506 12/1990  Calderwood ....................... 422/81 X
5,080,866  1/1992  Petty et al. ............................ 422/80

OTHER PUBLICATIONS

Haswell et al. "On-Line Microwave Digestion of Slurry Samples With Direct Flame Atomic Absorption Spectrometric Elemental Detection" Analyst, Feb. 1992, vol. 117.
M. Aoyagi et al. Analytica Chimica Acta, 214 (1988) 229-237.
Yukio Hirai. Analytica Chimica Acta, 115 (1980) 269-277.
Hinkamp and Schwedt, Analytica Chimica Acta, vol. 236, pp. 345-350 (1990): Determination of Total Phosphorus with Amperometric Detection, Etc.
Burguera and Burguera, Analytica Chimica Acta, vol. 179, pp. 351-357: Flow Injection and Microwave-Oven Sample Decomposition for Determination of Copper, Zinc and Iron, Etc.
Chen, Chiou and Wang, J. Chem. Soc. Chem. Commun., 1990, pp. 807-809: Preparative Scale Organic Synthesis Using a Kitchen Microwave Oven.

Primary Examiner—James C. Housel
Assistant Examiner—Maureen M. Wallenhorst
Attorney, Agent, or Firm—Raymond F. Kramer

[57] ABSTRACT

A continuous flow microwave heated digesting system, which is especially useful for digesting samples of materials to be analyzed with an atomic absorption spectrometer (ASS), includes a chamber, a source of microwave radiation into the chamber, thin bore chemical resistant an microwave transmissive tubing within the chamber onto which the microwave radiation impinges to heat contents of the tubing, and a pump or other suitable apparatus or device for passing through the tubing the sample of material to be digested, dispersed in a digesting medium for it, which sample in the digesting medium is in the form of a discrete slug in a carrier liquid. A suitable device is provided for inserting into the carrier liquid, which is usually water, the slug of material to be digested in the digesting liquid and a backpressure controller is also provided to control backpressure on the slug and the carrier liquid n the tubing. By such backpressure control the slug develops bubbles during the time it is being heated and condenses to liquid form upon cooling thereafter. The bubbling action aids digestion of the material to be digested but the bubbles ought to be condensed before analysis of the digested material by an AAS or other analytical apparatus. Such condensation is effected by a cooling apparatus and the digested material in the digesting liquid in the carrier is filtered by a special filter before being analyzed, which protects the backpressure controller and the AAS and improves AAS analytical results.

17 Claims, 6 Drawing Sheets

MICROWAVE HEATED DIGESTING SYSTEM FOR DIGESTING MATERIALS TO BE ANALYZED

This invention relates to a continuous flow microwave heated digesting system for digesting materials to be analyzed. More particularly, it is of such a system wherein a slug of such a material in a digesting medium is inserted into a carrier liquid, passed through a thin walled tube which is exposed to microwave radiation while a backpressure is maintained on it, and is then cooled, filtered and passed directly to an atomic absorption spectrometer or other suitable instrument for analysis.

Before the present invention microwave radiation had been suggested for use in heating materials to be digested and it had also been suggested that flow injection analysis could be employed wherein a sample to be analyzed could be added as a slug in a digesting fluid, such as an acid, to a carrier stream, such as water, heated by microwave radiation and analyzed by atomic spectrometry. Such disclosures are in 179 Analytica Chimica Acta 351-357 (1986), 5 J. Flow Injection Analysis, No. 2, 121-131, J. Chem. Soc. Chem. Commun. 807-809, and 236 Analytica Chimica Acta 345-350 (1990). However, such references do not describe the present apparatus and process and, in particular they do not describe applicants' use of backpressure regulation, filtration, mechanism (bubbling to promote digestion) and specifics.

In accordance with the present invention a continuous flow microwave heated digesting system comprises a chamber, a source of microwave radiation directed into the chamber, a long, thin bore chemical resistant and microwave transmissive tube in the chamber onto which the microwave radiation impinges so as to heat contents thereof, means for passing through such tube material to be digested, in a slug of a liquid digesting medium therefor, in a carrier liquid, cooling means, to cool the carrier liquid, digesting medium and material digested after such had been microwave heated, and backpressure means to maintain a backpressure on the tube contents, to prevent excessive distribution of the material and digesting medium in the carrier, so that such material is digested in the tube within a time in the range of 5 seconds to 10 minutes. Also within the invention are a process for analyzing a material, in which the described digesting system is employed, and an apparatus or system in which a certain type of filter is present to protect the backpressure regulating means and to prevent insolubles from being transmitted to an analytical apparatus, such as an atomic absorption spectrometer (AAS).

The invention will be readily understood by reference to the appended drawing, in which.

Figure 5:
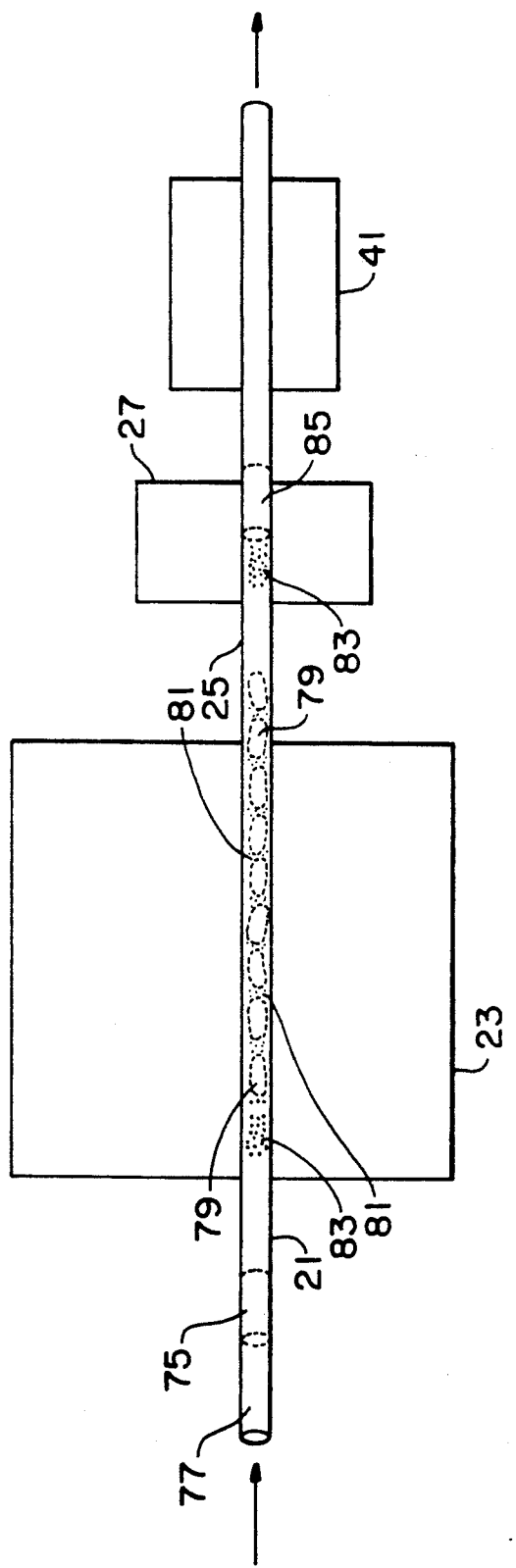
Figure 6:
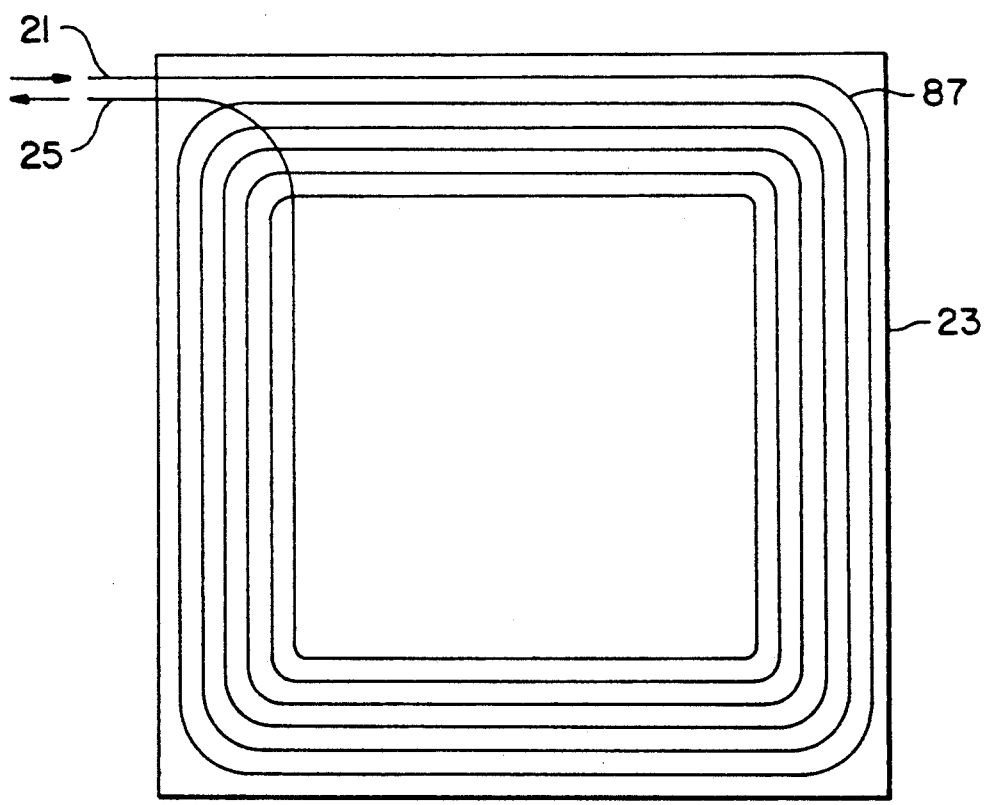

FIG. 5 is a schematic illustration of an elongated slug of material to be digested in digesting medium, in a carrier liquid, passing through the microwave heating unit, the cooler and the back-pressure regulator, to the AAS, omitting the filter and the pressure sensor, showing slug expansion and contraction due to controlled bubbling and condensation respectfully; and FIG. 6 is a plan view, schematically illustrated, of a position in a microwave chamber of the tubing or passage for the carrier and material undergoing heating and digestion.

Figure 1:
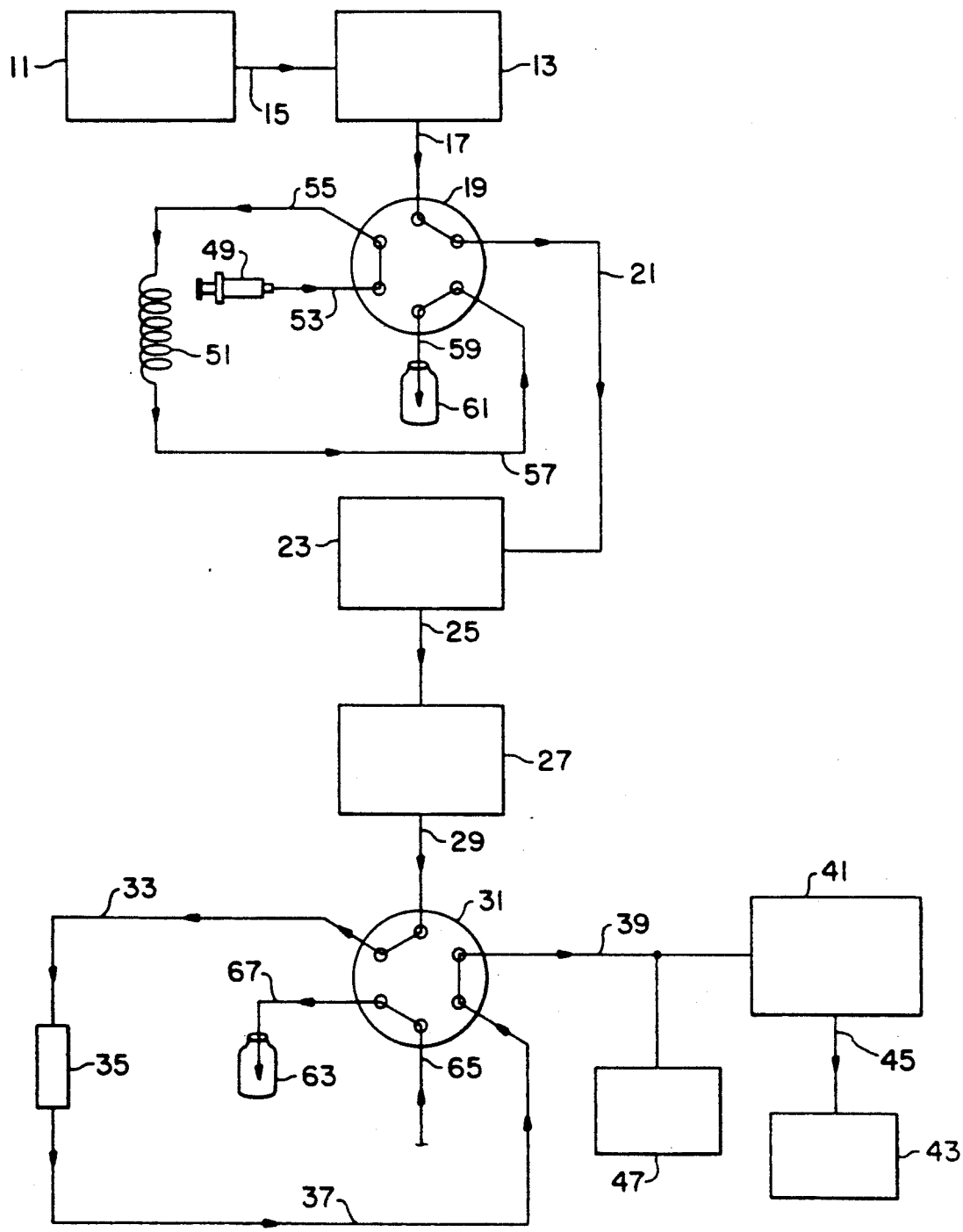
FIG. 1 is a flow diagram of the digestion system of the invention, illustrating continuous flow of carrier liquid that contains a slug of material to be digested in a digesting medium (not specifically shown in this view) being passed through the invented digestion apparatus to an atomic absorption spectrometer, which measures the contents in the sample of various elements.

In FIG. 1 carrier reservoir 11 (which usually contains water, the preferred carrier) is shown communicating with pump 13, which provides the motive force to drive the carrier and the contained slug of material to undergo digestion in the digestion medium through the system. Line or tube 15 connects the reservoir and the pump and line 17 connects the pump to a multi-position Rheodyne ® valve 19. In the position of the valve illustrated the carrier passes through line or tubing 21 into microwave chamber 23, wherein the tubing is coiled in a substantially horizontal plane, and the contents thereof are subjected to heating by microwave radiation from a microwave source (not illustrated, but conventional magnetrons or other sources may be employed). The carrier and slug then pass through line 25 into a cooler 27 (preferably of the Peltier type) and then through line 29 to another Rheodyne valve 31, which, as illustrated, directs them via line 33 to filter 35 and then through line 37, valve 31 and line 39 to backpressure regulator 41 and finally to AAS 43 via line 45. Pressure sensor 47 is provided to indicate the pressure in the system. Also shown in FIG. 1 are sample addition means 49, shown as a syringe, a coil 51 of tubing, connecting tubing 53, 55, 57 and 59, valve 19 and waste container 61, the functions of which will be described later. A source of a flushing medium, such as water, which may be used to backflush filter 35, as illustrated in FIG. 3, is shown connected to waste container 63 by line 65, valve 31 and line 67.

Figure 2:
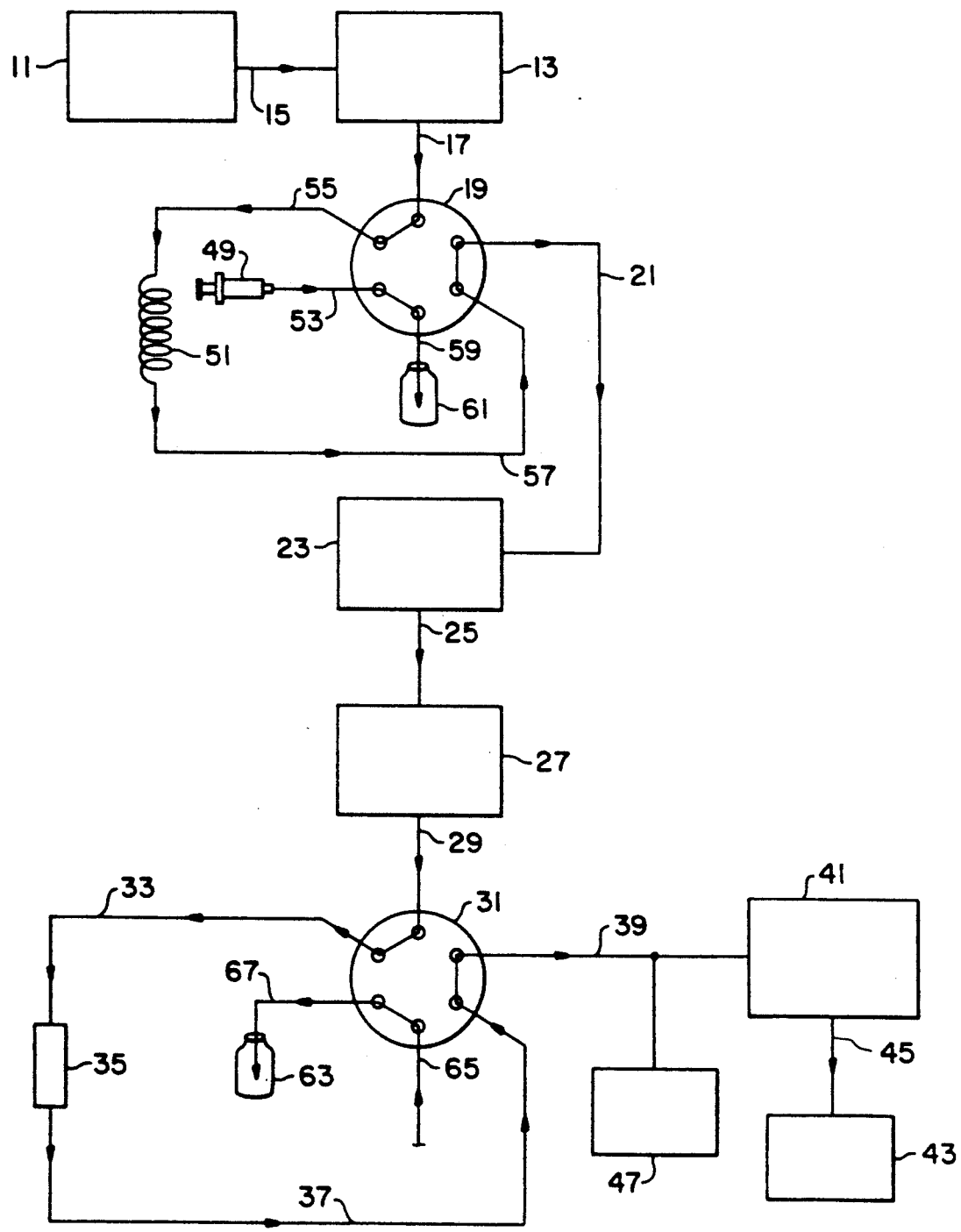
FIG. 2 is a flow diagram like that of FIG. 1, but with a valving change to insert the FIG. 1 slug of digesting medium, containing material to be digested, into the carrier stream.

In FIG. 2 the various parts of the system are the same as in FIG. 1, with the exception that the FIG. 1 slug of material to be digested, in its digesting medium, which was in coil 51 and lines 55 and 57, has been inserted into the carrier liquid by suitable adjustment of Rheodyne valve 19.

Figure 3:
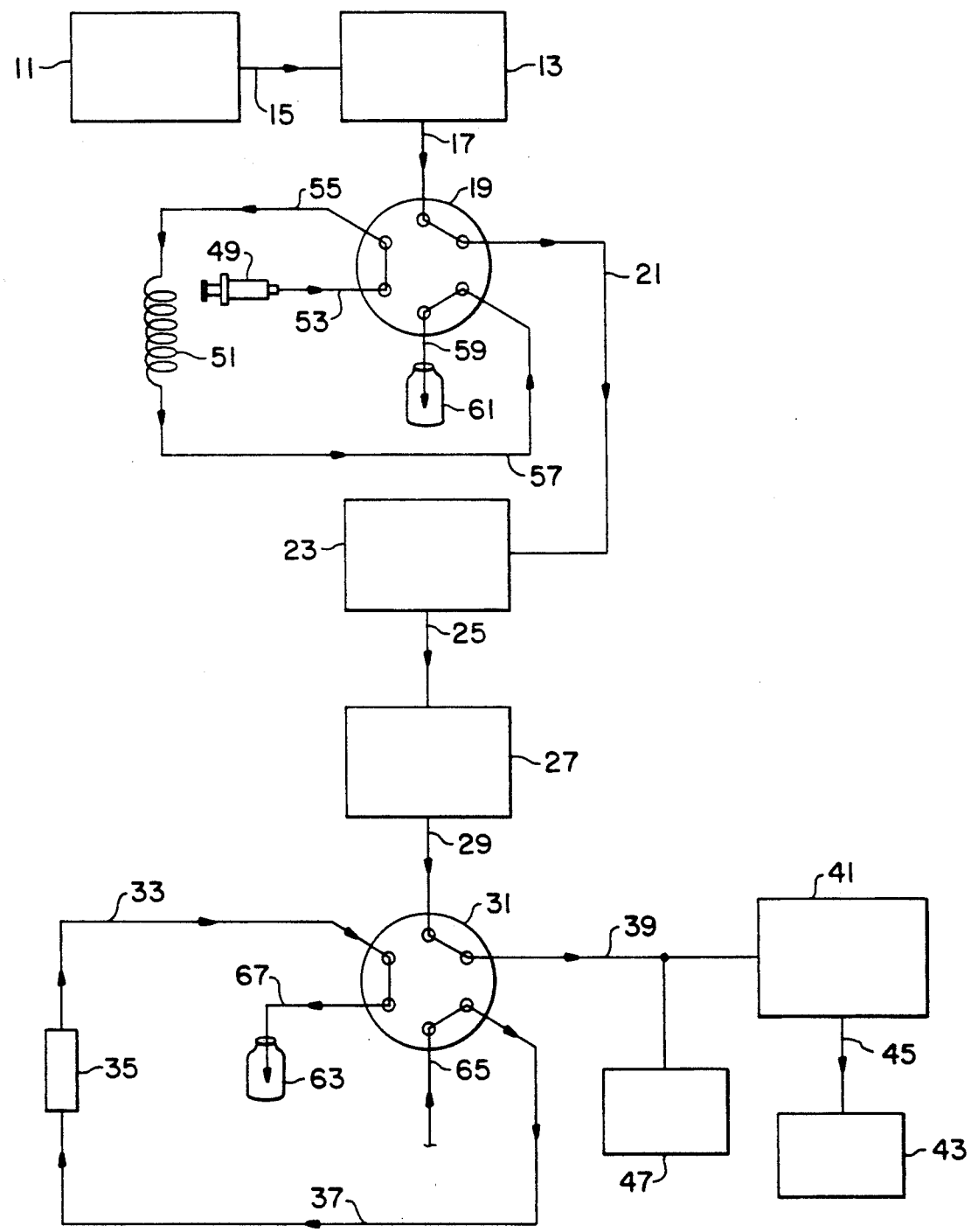
FIG. 3 is a flow diagram like that of FIG. 1 illustrating backflushing of a filter that protects the backpressure regulator and prevents insoluble material from entering the AAS.

In FIG. 3 the system parts are also the same as those shown in FIG. 1 but in FIG. 3 there is illustrated the backflushing mode, wherein flushing fluid (usually water) is passed through line 65, valve 31 and line 37 in reverse flow to filter 35, to release any solids therefrom, which are carried with the flushing liquid through line 33, valve 31 and line 67 to waste, as represented by waste bottle 63.

Figure 4:
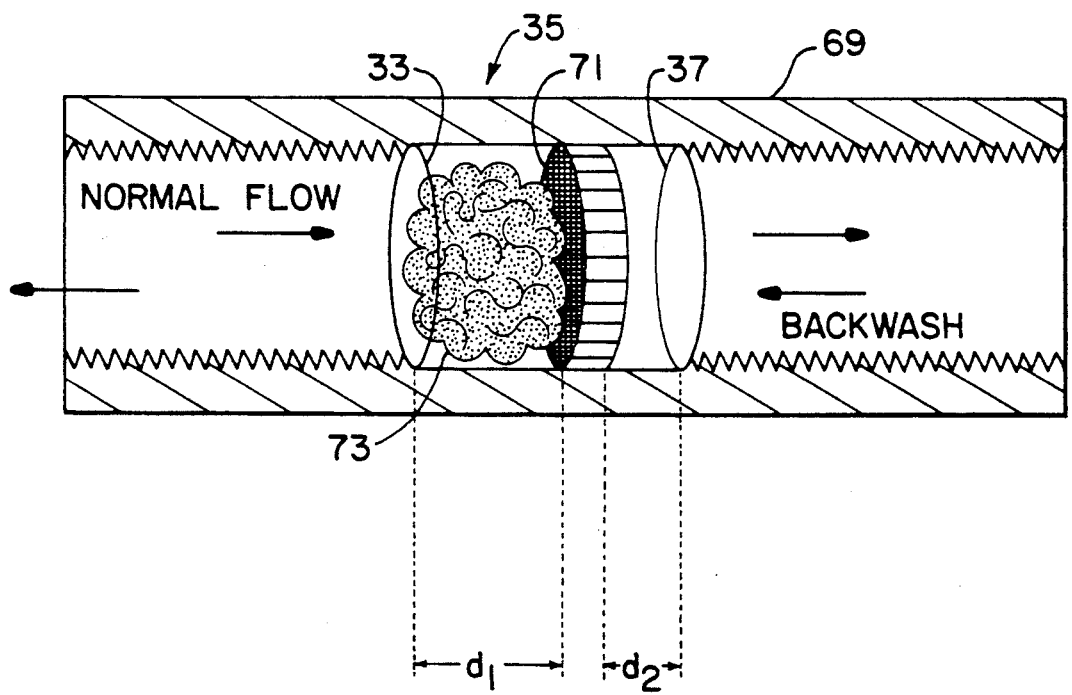
FIG. 4 is a partially cutaway and sectional elevational view of a filter of this invention joined to tubing through which the carrier and slug of material undergoing digestion pass, illustrating normal flow during digestion, and backflushing of the filter.

FIG. 4 illustrates filter 35, which includes collar means 69 adapted to fit onto tubes 33 and 37, a mesh or fritted filter member 71, of micron sized or somewhat larger openings hand spacings between the tubes and the filter member, designated $d_1$ and $d_2$, with the $d_1$ space being larger than the $d_2$ space and being filled with fine glass wool 73.

FIG. 5 shows a slug 75 of material being digested (including the sample to be analyzed in a digesting medium) in the tubing 21 after being injected into carrier 77 and before entering the microwave heating apparatus chamber 23. During heating in the microwave chamber the slug expands in size and changes in character due to vaporization of some of the digesting medium (such as water and nitric acid), forming bubbles 79, with digesting medium containing digested sample, designated by numeral 81, adjacent to such bubbles. Some undigested particulate material from the sample, designated by numeral 83, trails behind the expanded "slug" of bubbles 79 and medium 81 and after passage through tube 25 and cooler 27 such expanded "slug" contracts to slug 85, trailed by undigested particles 83. Such particles are removed from the carrier by filter 35 (not shown in FIG. 5 but illustrated in FIGS. 1-4), after which the slug passes through backpressure regulator 41 and thence to AAS 43 (not illustrated in FIG. 5) or other analytical means.

In FIG. 6 there is illustrated a preferred form of arrangement (coiling) of the narrow bore tubing, designated 87, in the microwave chamber 23. As illustrated, the tubing is coiled about the interior wall of the chamber in a concentric pattern but other patterns and locations may also be used. The tubing may be stacked, braided, woven, balled, randomly placed or otherwise positioned so long as the contents are satisfactorily heated. In some instances it may be desirable to coil the tubing about a plurality of vertical posts or members in the chamber in the manner that a hose is coiled on a reel. Of course, care will be exercised to avoid having any kinks in the tubing unless such are to be intentionally employed to create desired backpressure on the system (which can also be accomplished with pinch clamps).

The described system may be based on a microwave heating system or apparatus like any of those described in U.S. Pat. Nos. 3,909,598; 4,438,500; 4,565,669; 4,566,312; 4,566,804 or 4,651,285, but in the work reported herein there was employed a CEM Corporation microwave heating system that such company designates as their MDS 81. Such unit has a power rating of 600 watts and in the present work operates at 80 to 100% power, e.g., at 90% power, which is preferred.

Various types of pumps may be employed to force the carrier, digesting medium and sample (mixed in with the digesting medium) through the tubing or lines and the various valves and apparatuses. Peristaltic and gear pumps made of materials not adversely affected by the carrier medium are desirably employed because they are positive flow pumps and can maintain a desirable consistent flow rate through the system and to the nebulizer of the AAS against the backpressure of the system. In the present work there is employed an Ismatec ® MV-Z pump.

The tubing used in the microwave heating apparatus may be any such that will transmit microwave radiation through it and will also resist reaction with the digestion medium (and the sample and the carrier, too, of course). While the dimensions of the tubing will often depend on the characteristics of the sample material and the digesting medium, it has been found that the internal diameter (i.d.) of the tubing should usually be in a range like 0.3 or 0.5 to 2 mm preferably being in the range of 0.7 to 1 or 1.5 MM., e.g. about 0.8 MM, and the length thereof should usually be in the range of 5 to 50 meters, preferably 15 to 25 meters, e.g., about 20 meters in the microwave chamber. The overall tubing or line length, through which the sample passes, may be from 8 to 80 meters, preferably 20 to 50 meters, e.g., about 35 meters. Usually it is undesirable to employ tubing of an internal diameter less than 0.5 MM. because of possible blockages caused therein by the sample particles especially in the charging loop or coil. However, for easily digested samples and those which do not block objectionably such thinner bore tubing may be employed but even then it is best for the injection loop tubing to be of at least 0.5 MM. i.d. The preferred material of construction of the tubing is polytetrafluoroethylene (PTFE), such as Teflon ®, but glass, borosilicate glass, quartz and resistant plastics, such as polyethylene and polypropylene, may also be employed under the right conditions.

The injection loop of the system should be of appropriate capacity so that the system heats the sample and the digesting medium sufficiently to digest all or substantially all of the materials analyzed for in the digesting medium and it has been found that with a feed rate to the AAS nebulizer in the range of 2 to 10 ml/min., preferably 4 to 6 ml./min., such loop should be of 0.5 to 7.5 or 10 ml capacity, preferably 0.7 to 1.5 ml capacity, e.g., about 1 ml capacity. The greater capacities, such as 7.5 ml allow multiple elemental analyses of a single digested sample to the AAS, which multiple analyses require a longer continuous signal for a longer absorption period (to allow for beam frequency changes) Ideally, the mentioned capacity and bore allow about 1 to 3 minutes for the sample to pass through the system but such period can be varied, being 5 seconds to 10 minutes in some cases, and can be in the range of 10 seconds to 3 minutes. It is normally not preferred for the heating to take more than 3 minutes, since one of the main purposes of the present invention is to speed up the analytical procedure, while retaining accuracy, but for hard to digest material more time may be needed and easily digested samples can be digested more quickly.

The valve mechanism employed to facilitate syringe injection of the analytical sample and digestion medium into the system via the loop or coil 51 may be of other designs than that illustrated in the drawing but it is preferred to employ an Anachem 5020 Rheodyne two-way injection valve or equivalent for both the introduction of the sample and digesting liquid and for facilitating of backwashing. The backpressure regulator, which is important to the invention because it facilitates condensation of the digesting medium after cooling, and prevents excessive gassing of the medium and pumping problems that can be associated with that, may be of any suitable type in the circumstances and desirably maintains the pressure in the system in the range of 30 to 120 lbs./sq. in gauge, preferably 60 to 100 lbs./sq. in. g. e.g., 75 lbs./sq. in. gauge. A suitable regulator is that identified as Anachem P736. The cooler may be of relatively simple or sophisticated design. It is possible to employ a simple ice/water bath through which the tubing may be run after exiting from the microwave chamber. However, it is preferred to utilize thermoelectric heat pump cooling devices that utilize the Peltier effect, such as those available from Melcor, sold under the name Frigichip TM. The cooler will normally be effective to cool the liquid stream to a temperature in the range of 5° to 50° C. preferably 20° to 40° C. e.g., room temperature, which is usually in the range of 20° to 30° C.

The filter that is employed has been found to be especially effective in the described applications because it removes undigested particles (from which the digestible materials have been removed) from the digestion medium (containing digested material) without excessive pressure drop due to filter blockages and it does so effectively, allowing virtually no particles of objectionable size to pass through. The glass wool is of a denier like that of normal laboratory glass filter material but other glass wool products can also be utilized, and the material of construction can be changed to borosilicate glass or quartz, when that is desired, and in some cases polymeric plastic materials or mixtures of such with glass or quartz may be useful. The mesh or fritted filter means of the filter assembly will desirably have openings in the 20 to 100 microns range, preferably 40 to 60 microns range, e.g., 50 microns, and the material of construction may be glass or quartz frit or stainless steel (or any other suitable material). The length of the "glass wool section" ($d_1$) will normally be from 1.2 to 5 times that of the spacing downstream of the mesh or fritted filter ($d_2$), preferably 1.5 to 3 times that, e.g., about twice. It has been found that such most preferred proportions result in easier filtration and backflushing, and the glass wool holds its shape and volume and does not pack objectionably during use. Also, the mesh or fritted filter helps to maintain the glass wool filter element in desired position and the $d_2$ spacing facilitates better peripheral filtration and backwashing. The mentioned backflushing may be carried out by injection of backflushing water into the system with a syringe or by other suitable means, in conjunction with operation of the Rheodyne valve.

The pressure sensor or monitor 47 can be a conventional pressure gauge but is preferably an electronic device which digitally displays the pressure continuously. The AAS is one which continuously nebulizes the stream, including carrier and digestible material, with digesting liquid, desirably at a rate of about 4 to 6 ml/min., and reports and records the analyses. Such an AAS may be that sold under the trademark Thermoelectron 357. However, although an AAS is the preferred analytical device employed for analyzing the digested sample, it is possible to utilize the described digesting system to digest samples that are then analyzed with different analytical means, such as colorimeters, chromatographic instruments, infrared instruments, etc. When such other analytical instruments are employed the operations are very preferably continuous and results are computer reported but batch analyses are also feasible. Also, because the feed rates to such other instruments may be different from those to AAS's., it may be desirable for the operating conditions and for the constructions of the system elements to be changed accordingly. Thus, pumping rates, microwave power, tubing internal diameter, backpressure, cooling rate and other factors may be adjusted to compensate for different feed rates of sample to the analytical instrument.

Although it has not been illustrated in the accompanying drawing it is within this invention to utilize temperature control and flow control to regulate the digestion of the analytical sample. For example, a temperature probe may be located at an appropriate place, usually at the downstream end, of the heating tube, and power to the magnetron may be diminished if the temperature becomes too high, or the flow rate can be increased, assuming that such an increase is compatible with the digestion and with the analytical equipment being employed. Alternatively or additionally, the flow rate can be measured and the pump operation may be automatically controlled to maintain it at the desired rate, corresponding to that at which the digested material is being withdrawn for analysis. It is desirable for such control to be computerized and for monitors and printers to be present to display and record the readings, but such is not necessary.

The digestion process of this invention starts with dispersing in digesting medium the analytical sample to be analyzed by means of the AAS or other analytical apparatus. Such dispersion can be accomplished by weighing a sample and adding it to a known weight or volume of digesting medium. The sample to be analyzed may be any material capable of being digested and analyzed by the means at hand but usually the materials to be analyzed are organic materials such as foods, biological tissues and fluids, plants, wastes and environmental samples, or inorganic materials such as water samples, ores, coals, oil shales, sediments and paints or pigments. However, various other materials may also be analyzed and the analyses may be for different elements or compounds, although often the AAS analyses are for elements, such as metals, present in foods or other materials. The digesting medium employed may be any suitable such medium, including acids, bases, salts and solutions of such, with aqueous solutions usually being those of choice, which solutions are very often of strong acids, such as nitric acid, sulfuric acid, hydrochloric acid and perchloric acid, strong oxidizing agents, such as potassium permanganate, or strong reducing agents, such as stannous chloride and formaldehyde. For elemental analyses by AAS the digesting medium of choice is nitric acid and the present inventors have found that the concentration of such acid in water should be at least 5%. Such 5% lower limit is applicable to colorimetric analyses for phosphate and may also be used for some other analyses but for elemental analyses by AAS of various other organic and inorganic samples the desirable lower limit for the acid concentration is 8%. 10% or about 10%, or more, up to 30% is preferred, but about 10% is most preferred because digestion rates are not appreciably improved at higher concentrations, using this digestion system. Mixing of the aqueous nitric acid or other digesting medium and the sample to be analyzed may be effected in normal manner, as by employing a magnetic stirrer in which the stirring magnetic element is coated with PTFE (Teflon) or other protective coating that is non-reactive with the digesting medium. Prior to mixing, the sample is size reduced to particles which are preferably no larger than 180 microns in diameter. After the sample is uniformly mixed in with the digesting medium, usually with the concentration of the sample in the medium being in the range of 0.005 to 0.5%, by weight, or weight (grams) per volume (ml), at which concentration the suspension is non-separating for hours, it is taken up in a syringe which will hold more than the amount needed to fill the system coil or loop. Normally the sample concentration is chosen to contain enough sample, usually at least 25 mg for the analysis, without forming an objectionably thick slurry, which can occur at concentrations greater than 1%. Also, using higher concentrations and/or larger sample particle sizes can cause blockages of the coil or of holes in the Rheodyne valve switching plate, which could result in false analyses. The suspension in the syringe is then injected into the charging loop, which is preferably of about 1 ml capacity. Syringe injection is employed in this procedure but it may be replaced with a pump and auto-sampler combination in a more highly automated embodiment of the invention. The main pump 13 is then activated and the carrier liquid, which is usually water, is pumped through the system as previously described, the 4-way Rheodyne valve is changed its other position (used as a 2-way valve) and the 1 ml slug of sample suspension is inserted into the stream of carrier flowing through the system. The carrier and suspension or thin slurry are both normally at about room temperature when charged to the system but during passage through the microwave chamber in the thin tubing the temperature thereof may be raised to as high as 100° or 110° C. or whatever upper limit can be withstood by the tubing and backpressure regulator, with respect to both pressure and temperature, and it is possible, with resistant tubing and the use of superatmospheric pressure on the suspension, to operate at a temperature as high as 140° C. and at pressures up to 200 lbs./sq. in. g.

When the digesting system is directly connected to an AAS that nebulizes about 5 ml/min. of digestate (digested sample in digesting medium) the pumping action will be controlled so that the digestate forced through the system is fed at that rate. For a system that includes in the microwave chamber 20 meters of 0.8 MM. inside diameter tubing and the equivalent of an additional 15 meters of such tubing external to such chamber, the stream speed is about 20 m/min. and the time in the system is about 1½ to 2 minutes, with the time in the heating tubing being about one minute (or 30 seconds to 2 or 3 minutes). The tubing size is chosen so as to carry the slug of digestate (or digesting liquid and sample) through the heating system at the correct feed rate to the analyzer and at a rate at which it will be heated sufficiently in the microwave chamber to digest it completely (or essentially completely). Such tubing size should also be that at which the bubbles of water or digesting medium that form during heating desirably expand to about 2 to 10 times the original slug length, preferably 2 to 5 times such length, at which expansion good digestion results. It is theorized that the improved digestion noted results from the mixing action effected and from new contact surfaces exposed when the bubbles are formed and when they move with respect to the liquid (and solid particle) bounding materials, thereby promoting better contacts between the sample and the digesting medium. However, that theory has not been completely verified so applicants are not bound by it.

When other analytical equipment is being employed or when the digested material is being subjected to batch analysis, so flow rates are not relevant, other velocities through the heating tubing in the microwave chamber may be utilized. However, the AAS analyzer lends itself to ready analyses for a number of different elements in the same slug of digestate, providing that the slug is of sufficient size. Also, continuous analyses, like that described, protect the digestate against contamination, transfer losses, chemical reactions and weighing and measuring errors, and therefore are much preferred.

After passage through the heating passageway in the small bore tubing in the microwave chamber the tubing and contained digestate (and some undissolved parts of the sample, from which the digestible materials [analytes] have been removed) pass through the cooler and are cooled to approximately room temperature or a little above, in most cases. Cooling will normally be to the range of 5 to 50° C. and preferably is to 20° to 30° C.

In the cooling operation the bubbles of water vapor and digesting medium, if volatile, will be condensed to liquid and will reform the digesting liquid into an essentially continuous slug of liquid again, in a stream of carrier liquid. Such cooling is important because the presence of bubbles in the slug can interfere with operation of the analytical equipment, such as the nebulizer of the AAS, and can cause false results.

After cooling the slug and carrier to about room temperature and having the slug again become a unified liquid, with no bubbles in it or separating parts of it, it and the carrier stream are passed through the filter, which removes essentially all particles of a diameter (or equivalent diameter) of 50 microns or more. Such removal protects the backpressure regulator and the AAS nebulizer, when employed, and ensures that the absorption pattern of the AAS or the readings of other analytical instruments, when employed, will be consistent and accurate, and will not be affected by false readings caused by the presence of the particulate materials in the digestate. Ideally, the filter will remove particles as small as 5 microns and less from the digested liquid but when the particle sizes are no larger than 50 microns it is found that the AAS and other analytical instruments of the types mentioned previously herein will be accurate (often within about 1% of the amounts of the elements actually present).

The backpressure regulation will be to the ranges previously mentioned, with the main consideration being to coordinate such regulated pressure with the other operating conditions of the system so as to make the flow through the system consistent and at the desired rate and to have the heated slug develop bubbles therein which expand its volume to the extent previously disclosed, while contracting it completely to original size on cooling. Although the operations are controlled as desired there may be noted some particles of samples which are undigested, usually at the trailing interface between the digesting liquid and the carrier, due to the lower concentration of the digesting medium at such location, where it has been mixed to some extent with the carrier, but such particle usually have had enough of their extractable elements removed from them or they are small enough so that their removal from the slug delivered to the analyzer does not adversely affect the results of the analysis. Also, during flow through the tubing the essentially laminar flow, especially of the portion of the cooled slug in contact with the tubing wall, causes a trailing edge effect which changes the absorption curve or reading but such changed reading should be ignored and the reading to be taken should be that for the main section of the slug's atomic absorption pattern (or pattern for other analytical instrument).

It is desirable for the filter to be backwashed after every use of the equipment but in some cases, as when replicates of the same sample material are being analyzed (or prepared) experience may show that less frequent backwashings will suffice without causing any problems. In some instances, as when several such samples are passing through the heating section at the same time, with sufficient carrier between them, it may be difficult to backwash between samples and it may be found to be unnecessary to do so.

The AAS typically takes up the sample to be tested by aspiration into the nebulizer but other means for charging it can also be employed, including positive pump feeding. The AAS preferably includes a display to show the extent of the absorption of the characteristic wavelength that is characteristic of the particular element for which the sample is being analyzed and it is desirable that the results be computer recorded and stored too. Several such elements may be tested for in the same sample slug by utilizing different emitters of such different characteristic wavelengths (for different metals). Alternatively, several replicates can be run and the results can be averaged for a particular element and then a new sample of the same material may be tested for another element, in the same general manner. Instead of running the digestate directly to analytical equipment it may be collected in a manner that separates it from the carrier, and may then be used for batch analyses.

In variations of the invention, temperature, pressure and flow rate controls may be employed to control the system and the digestion processes. A less polar liquid carrier than water may be employed as a carrier provided that it has acceptable mobility and vapor pressure characteristics and does not merge with the digesting medium or react with it or the sample material. A plurality of streams of carriers, digesting media and samples may be passed through the same microwave chamber at the same time, using the same coolers but different filters, backpressure regulators and analyzers. The invention may also be used to promote chemical reactions, with the reactants replacing the sample and digesting medium in a carrier or replacing the carrier, too, in which latter case the reactants are first mixed and then charged to the pump and pumped through the apparatus. In such reactions the backpressure will be controlled as previously described to produce the desirable bubbling on heating and coalescing on cooling. In a further innovation the whole system and process may be computer controlled with respect to coordinating pumping rate, sample injection, magnetron power applied, filtration, backpressure application, AAS or other analyzer operation and reporting of results. Thus, ultimately, the system can involve little operator attention and yields excellent results, as has been proven by comparisons with standard test specimens. Such specimens may be employed to standardize the system initially and periodically the results may be checked against such standards, too.

The advantages of the invented system and processes are significant. It is fast, contamination-free, involves little operator supervision, requires few weighings and transfers, can operate with little sample, can run replicates easily, requires relatively simple and inexpensive equipment, with the exception of the AAS, involves little heating hazard to operators, because the heating chamber is enclosed, releases little noxious fumes, except at the normally hooded AAS, where they are safely removed, and yields accurate analyses, which may be observed on a display or may be computer printed and stored or processed.

Previous flow injection analyzers have not incorporated the backpressure controllers utilized in the present invention and have not included filters like that of this invention so the results obtained by such processes were not as good as those from the present invention. The present results are more accurate and the samples that are tested are digested more rapidly due to the unique bubbling and coalescing actions described, and due to removal of any undigested particulate materials which may be present. Thus, the present invention is superior in speed and accuracy, two of the main objectives of analyses.

The following examples illustrate but do not limit the invention. Unless otherwise indicated all parts are by weight and all temperatures are in °C.

EXAMPLE 1

The apparatus employed in this example is that illustrated in the drawing (all figures) with the pump being an Ismatec MV-Z positive displacement pump, the microwave heating apparatus being A CEM Corporation MDS-81, containing 20 meters of 0.8 mm. inside diameter polytetrafluoroethylene (PTFE) tubing positioned in a horizontal coil in the microwave chamber, the injection loop or coil being of a volume of one ml. and being equipped with a Rheodyne (Anachem 5020) injection valve, the cooling means being a 5 meter length of the PTFE tubing in an ice/water mixture, the filter being of 50 microns stainless steel mesh and being 4 mm. in diameter, with a $d_1/d_2$ ratio of about 2.5, and with the packing in the $d_1$ section being glass wool of about 0.1 mm. in diameter, the pressure sensor being a CEM Corporation sensor, the backpressure regulator being an Anachem P-736, which is set at 75 lbs./sq. in. g., and the AAS being a Thermoelectron 357 unit. The same PTFE tubing was employed throughout the system for all couplings and loops. The analyses by the AAS were recorded by a Linseis LS-52 chart recorder and a magnetic stirrer was employed for initial mixings, prior to entry of the sample and digesting medium into the system, which stirrer had a stirring element that was coated with PTFE.

The digesting medium was nitric acid of analytical reagent grade, supplied by BDH (Poole) and the water was distilled and deionized. Reference samples for digestion and analyses were standards obtained from the National Institute for Environmental Studies (Japan) with the exception of the bovine liver, which was obtained from the National Institute for Standards and Technology (their SRM 1577a). Such samples were employed in amounts of at least 25 mg. and at concentrations in the range of 0.005 to 0.5% w/v (g./ml.) in the digesting medium, e.g., 0.01%, and the sample is of particle sizes that are all below 180 microns in diameter. The concentration of sample in the digesting medium is kept below 1% to avoid occurrence of blockages in the tubing.

Initially, a metal salt of known metal content, in this case a magnesium salt, is mixed with the 10% nitric acid at a concentration of 0.001% and is passed directly to the nebulizer of the Thermoelectron 357 AAS, and the magnesium content is read. Then a 1 ml. portion of the same mixture is passed through the invented system described herein and the magnesium content is read. Correlations are essentially perfect, with the correlation coefficient for the sample passed through the invented system being 0.9999. On the basis of this experiment, and others like it for other metals, such as calcium, zinc and iron, the various samples of materials were analyzed by the invented procedures and results were compared to actual metal contents thereof, as had been established by the agencies which originated the samples, by accepted analytical methods.

A dispersion of about 0.01 g./ml. of Chlorella is made in 10% aqueous nitric acid and is injected into the invented system in the manner previously described, with distilled and deionized water being used as a carrier, with the water, nitric acid and sample being at room temperature (about 25° C.), and with the Chlorella particles being less than 180 microns in diameter. The microwave heating apparatus is operated at 90% of full power, at 540 watts, and heats the digesting medium to 105°-120° C., causing the production of bubbles therein, and the spreading out of the digestate "slug" in the carrier. The digesting medium, being a better coupler of microwave energy than the water carrier, is heated more by the microwaves and therefore can produce bubbling of the analyte without bubbling in the carrier, which carrier will be at a lower temperature. It is normally desirable but it is not essential, to avoid any bubbling of the carrier liquid. After passing through the heating section of the apparatus, which takes about ten seconds, the stream of digestate slug and carrier is cooled in the ice/water mix (but a Peltier cooler or other suitable cooling means may also be used) to about room temperature, is filtered, which removes any 50 micron and greater particles, and is fed through the backpressure regulator to the nebulizer of the AAS, wherein the absorption of relevant magnesium characteristic wavelength radiation is measured and recorded and the percentage of the magnesium is displayed and recorded. Similar runs are made, also with such chlorella sample being digested, and the percentages of calcium, zinc and iron present in it are reported. The described runs were repeated several times, desirably to a total of ten, and the mean values were calculated, together with the relative standard deviations.

The described procedures were repeated with mussel, sargasso, tea leaves, pepper bush and bovine liver samples, with some adjustments of system conditions, such as concentrations in the digesting medium, within the ranges given herein, to promote better heating and flow properties, and the percentages of magnesium, calcium, zinc and iron were recorded. Table 1 gives the concentrations (g./ml.) of test sample in 10% aqueous nitric acid for the various samples employed and for the different metal analyses.

TABLE 1

| Sample | Metal Analysis Magnesium | Calcium | Zinc | Iron |
|---|---|---|---|---|
| Chlorella | 0.01 | 0.01 | — | 0.2 |
| Mussel | 0.01 | 0.01 | 0.5 | 0.5 |
| Sargasso | 0.005 | 0.005 | — | 0.4 |
| Tea Leaves | 0.01 | 0.01 | — | — |
| Pepper Bush | 0.01 | 0.01 | 0.2 | 0.5 |
| Bovine Liver | 0.01 | — | 0.5 | 0.5 |

In Table 2 are given the analyses and relative standard deviations for analyses of the test samples. The analyses are given on the bases of percentages of known analyses, as reported by the authority from which the test samples originated, which are given in the table as either percentages, by weight, or as micrograms per gram, under the heading Act. (for actual), and it will be apparent which is intended (figures over 10 being for microns/g.).

TABLE 2

| | Metal | | | | | | | | | | | |
|---|---|---|---|---|---|---|---|---|---|---|---|---|
| | Magnesium | | | Calcium | | | Zinc | | | Iron | | |
| Sample | Anal. | Act. | RSD | Anal. | Act. | RSD | Anal. | Act. | RSD | Anal. | Act. | RSD |
| Chlorella | 96.3 | 0.33 | 2.3 | 99.0 | 0.49 | 3.1 | ND | 20.5 | — | 97.5 | 0.185 | 1.5 |
| Mussel | 97.2 | 0.21 | 1.4 | 100.0 | 0.13 | 7.6 | 102 | 106 | 7.0 | 96.8 | 158 | 4.0 |
| Sargasso | 102 | 0.67 | 0.9 | 93.8 | 1.41 | 1.9 | ND | 16.4 | — | 95.4 | 187 | 3.3 |
| Tea Leaves | 101 | 0.15 | 2.4 | 87.0 | 0.32 | 3.7 | ND | 33 | — | ND | — | — |
| Pepper Bush | 96.5 | 0.41 | 0.8 | 103 | 1.38 | 1.9 | 93.6 | 340 | 0.7 | 98.0 | 205 | 3.0 |
| Bovine Liver | 94.0 | 600 | 4.5 | ND | 120 | — | 95.9 | 123 | 0.7 | 107 | 194 | 4.3 |

Note
RSD = Relative Standard Deviation;
ND = Not Determined.

The analyses by the invented method are all considered to be satisfactory and accurate enough to warrant acceptance of the method.

In variations of the experiment of Example 1 digestions of other samples of materials to be analyzed, such as environmental specimens, wastes, ocean floor sediments, paints, pigments, waters and scales deposited from boiler waters, coals, oil shales, ores, plants, body tissues and fluids and various other materials of similar and different sorts, when digested by the process and with the apparatuses of this invention are suitable for analyses, by the AAS or other analytical means, such as colorimetric or chromatographic analytical means.

EXAMPLE 2

The processes of Example 1 are repeated but instead of employing the microwave heating apparatus, the CEM MDS-81 at 90% power (540 watts) power settings are changed to 50%, 80% and 100 and the extents of digestions are noted by filterings of the digestates (containing some undigested materials) and comparisons of the amounts undigested. It is found that when 100% of power (600 watts) are employed satisfactory digestion is obtained but it is no better than for the 540 watt experiment of Example 1. When the powers employed are 300 watts (50% power) and 480 watts (80% power) the digestions are measurably less complete, and are generally considered to be unsatisfactory. However, satisfactory digestions can be obtained at such lower power levels by increasing the residence times in the microwave chamber but that lengthens the time needed for digestion, and it is an object of the present invention to speed up the digestion process.

EXAMPLE 3

The processes of Example 1 are repeated but instead of employing 10% aqueous nitric acid as the digesting medium other concentrations thereof are substituted, 5%, 20% and 30%. It is found that 5% is unsatisfactory but the 20% and 30% media digest the samples satisfactorily, but not significantly better than the 10% nitric acid. Accordingly, to avoid the need to use the more concentrated acids, which are more corrosive and more dangerous to handle, the 10% acid is that of choice. It is especially preferred when a surfactant is employed with the acid to promote better contact between the sample and the digesting medium. Surfactants such as $C_{12-18}$ linear alkylbenzene sulfonic acid, Turkey Red oil and Neodol ® 25-3 (Shell Chemical Co.) are more stable in the presence of lower concentrations of nitric and other digesting acids than in the presence of more concentrated acids and digesting media.

EXAMPLE 4

The apparatus employed in carrying out the process of Example 1 is changed by replacing the 0.8 mm. i.d. tubing with 6.5 meters of 0.3 mm. inside diameter tubing but the injection loop tubing is kept at 0.8 mm. i.d. to prevent blockages therein. The digested materials are then analyzed by colorimetric means directly attached to the exit tubing from the backpressure regulator. Satisfactory analyses are obtained but when the loop is also of 0.3 mm. i.d. tubing the results are unsatisfactory due to blockages of the loop or coil with particulate matter. When the i.d. of the tubing is greater than about 2 mm. the desired type of bubble formation in the digesting medium and contained digestible sample is not obtained so that although the residence time in the system is greater the digestion is not as even and the analyses are not as accurate. Similar unacceptable results are obtained when the backpressure regulator is removed from the system, which allows excessive bubble formation and can even cause "vapor lock" of the pumping means, together with inaccurate analyses.

EXAMPLE 5

The first chlorella experiment of Example 1 is run again ut with the 20 meters of 0.8 mm. tubing being rolled into a ball instead of being looped or coiled. The analysis for magnesium is less accurate than for the previously reported experiment, apparently due to irregular flow of material through the ball, possibly due to kinking therein or due to overly sharp changes of directions therein. From this experiment it is clear that it is desirable for the tubing to be positioned so that the liquid passing through it changes directions gradually and it also appears that it is undesirable for much of the tubing to be shielding other sections thereof from the microwave radiation that is desirably directed onto the analyte within the tubing. To avoid comparatively sharp directional changes in liquid flow, therefore, one usually will avoid tubing patterns of the ball, woven, knitted and crosshatched types, although with easily digested samples of very small particle sizes such may be feasible.

The invention has been described with respect to several illustrations and working embodiments thereof but it is not to be considered as being limited to those, because one of skill in the art, with the present specification before him or her, will be able to utilize substitutes and equivalents without departing from the scope of the invention.

What is claimed is:

1. A continuous flow microwave heated digesting system, useful for digesting samples of materials to be analyzed with an atomic absorption spectrometer, said system comprising a chamber, a source of microwave radiation directed into the chamber, a microwave transmissive tube extending through said chamber such that microwave radiation from said source impinges onto said tube so as to heat contents thereof, said tube contents including material to be digested in a slug of a microwave heatable liquid digesting medium, said slug being located within a carrier liquid in the tube, means for passing through the tube the carrier liquid with the slug of liquid digesting medium containing the material to be digested disposed therein, said tube further extending through a cooling means located downstream of said chamber to cool the carrier liquid and the contained slug of liquid digesting medium and material to be digested after such have been microwave heated and have exited the chamber, and backpressure regulating means to maintain a backpressure on the tube contents such as to allow controlled bubbling of the digesting medium in the tube in said chamber while it is being heated which promotes digestion of the material to be digested in the digesting medium while also ensuring condensation of said bubbles in said tube in said cooling means so that the material to be digested is digested in the tube in the chamber within a time in the range of about 5 seconds to about 10 minutes.

2. A digesting system according to claim 1 wherein said tube further extends upstream of said chamber where a multi-position valve means is located and wherein said multi-position valve means injects a measured slug of a digesting medium containing a material to be digested into a carrier liquid in the portion of the tube located upstream of said chamber.

3. A digesting system according to claim 1 wherein the microwave transmissive tube within the chamber is cylindrical, is of an internal diameter in the range of 0.3 to 2 mm and is of a length in the chamber in the range of 5 to 50 meters, and the means for passing through the tube the carrier liquid with the slug of liquid digesting medium containing the material to be digested contained therein is a pump, which pumps the carrier liquid and the contained slug of digesting medium containing the material to be digested at such a rate that said slug remains exposed to the microwave radiation for a time in the range of 5 seconds to 10 minutes which is sufficient to digest the material to be digested int eh digesting medium.

4. A digesting system according to claim 3 wherein the tube in the chamber is cylindrical, is of polytetrafluoroethylene and is substantially horizontally wound in a coil.

5. A digesting system according to claim 3 wherein the tube in the chamber is of an internal diameter in the range of 0.7 to 1.5 mm and is of a length in the range of 15 to 25 meters and the pump for pumping the material to be digested, the digesting medium and the carrier liquid pumps at a rate such that the material to be digested, the digesting medium and the carrier liquid are exposed to microwave radiation for a time in the range of 0.5 to 2 minutes.

6. A digesting system according to claim 5 wherein the tube is of an internal diameter of about 0.8 mm and is about 20 meters long.

7. A digesting system according to claim 3 wherein injection means and valving are located outside the chamber and upstream of the tube therein for injection of material to be digested, in a liquid digesting medium therefor, into the carrier liquid being pumped through the tube in the chamber.

8. A digesting system according to claim 7 wherein the cooling means is located outside the chamber and downstream of the tube therein and is capable of cooling the slug of digesting medium and the carrier therefor after digestion of the material being digested to a temperature in the range of 5° to 50° C., and the backpressure regulating means is located outside of the chamber, downstream of the tube therein and downstream of the cooling means, and is capable of maintaining a backpressure on contents of the tube in the chamber in the range of 30 to 120 pounds per square inch.

9. A digesting system according to claim 8 wherein a backflushable filter is located downstream of the cooling means and upstream of the backpressure regulating means.

10. A digesting system according to claim 9 wherein the backflushable filter is of a combination of a mesh or fritted filter means, which has openings in the size range of 20 to 100 microns, and glass wool, said glass wool being located upstream of said mesh or fritted filter means, and wherein a multi-position valve is located outside the chamber between the cooling means and both the backflushable filter and the backpressure regulating means, said multi-position valve selectively allowing flow of the slug and carrier liquid directly to the backpressure regulating means thereby bypassing the backflushable filter or allowing backflushing of the filter with a backflushing liquid before the slug and carrier liquid reach the backpressure regulating means.

11. A digesting system according to claim 8 wherein there is analytical means located outside the chamber and downstream of the cooling means and the backpressure regulating means for analyzing material digested in the tube in the chamber.

12. A digesting system according to claim 11 wherein the analytical means is an atomic absorption spectrometer, to which the carrier liquid with the slug of liquid digesting medium containing the digested material is fed directly from the backpressure regulating means.

13. A continuous flow microwave heated digesting system, useful for digesting samples of materials to be analyzed with an atomic absorption spectrometer, said system comprising a chamber, a source of microwave radiation directed into the chamber, a microwave transmissive tube extending through said chamber such that microwave radiation from said source impinges onto said tube so as to heat tube contents, said tube contents including material to be digested in a slug of microwave heatable liquid digesting medium, said slug being located within a carrier liquid in the tube, means for passing through the tube the carrier liquid with the slug of liquid digesting medium containing the material to be digested disposed therein, said tube further extending through a cooling means located downstream of said chamber to cool the carrier liquid and the contained slug of liquid digesting medium and material to be digested after such carrier and slug have been microwave heated and have exited the chamber, and backpressure regulating means to maintain a backpressure on the tube contents such as to allow controlled bubbling of the slug in the tube in the chamber while said slug is being microwave heated which promotes digestion of the material to be digested in the digesting medium while also ensuring condensation of said bubbles in said tube in said cooling means and maintaining a flow rate within said tube such that the material to be digested may be digested in the tube in the chamber.

14. A digesting system according to claim 13 wherein the cooling means and backpressure regulating means are located outside the chamber downstream thereof.

15. A digesting system according to claim 14 wherein the slug n the tube in said chamber bubbles and expands to a length which is 2 to 10 times the original length thereof during microwave heating of the tube contents.

16. A digesting system according to claim 15 wherein the cooling means is located upstream of the backpressure regulating means and is capable of cooling the slug and carrier liquid to a temperature at which said slug and carrier liquid are in a liquid state so that said slug and carrier liquid will be in said liquid state when said slug and carrier liquid pass through the backpressure regulating means.

17. A digesting system according to claim 16 wherein the tube inside the chamber is of an inside diameter in the range of 0.3 to 2 mm and is of a length in the chamber in the range of 5 to 50 meters, the residence time of the slug in the tube in the chamber is in the range of 5 seconds to 10 minutes, the backpressure maintained by the backpressure regulating means is as high as 200 lbs./sq. in. and the temperature to which the slug is raised is as high as 140° C.

* * * * *